(12) United States Patent
Bose (10) Patent No.: US 11,412,832 B2
(45) Date of Patent: Aug. 16, 2022

(54) COSMETIC APPLICATOR WITH ROTATABLE APPLICATION SURFACE

(71) Applicant: Toly Management Ltd., Zejtun ZTN (MT)

(72) Inventor: Rahul Bose, New Dehli (IN)

(73) Assignee: Toly Management Ltd., Zejtun (MT)

( * ) Notice: Subject to any disclaimer, the term of this patent is extended or adjusted under 35 U.S.C. 154(b) by 0 days.

(21) Appl. No.: 17/158,281

(22) Filed: Jan. 26, 2021

(65) Prior Publication Data

US 2021/0244158 A1   Aug. 12, 2021

(30) Foreign Application Priority Data

Feb. 12, 2020   (IN) .............................. 202011005990

(51) Int. Cl.
*A46B 11/00* (2006.01)
*A45D 34/04* (2006.01)
*A45D 40/26* (2006.01)

(52) U.S. Cl.
CPC ......... *A45D 34/041* (2013.01); *A45D 34/045* (2013.01); *A45D 34/046* (2013.01); *A45D 40/261* (2013.01); *A45D 40/265* (2013.01); *A45D 40/267* (2013.01); *A45D 2200/1009* (2013.01)

(58) Field of Classification Search
CPC .. A45D 34/041; A45D 34/045; A45D 34/046; A45D 40/261; A45D 40/265; A45D 40/267; A45D 2200/1009
See application file for complete search history.

(56) References Cited

U.S. PATENT DOCUMENTS

| | | | |
|---|---|---|---|
| 2,034,416 | A | 3/1936 | Peat |
| 4,545,393 | A | 10/1985 | Gueret |
| 5,816,728 | A | 10/1998 | Nardolillo |
| 6,811,340 | B2 | 11/2004 | Petit |
| 7,429,141 | B2 | 9/2008 | Habatjou |
| 7,883,287 | B2 | 2/2011 | Thorpe |
| 7,959,369 | B2 | 6/2011 | Gueret |
| 8,151,807 | B2 | 4/2012 | Holloway |
| 9,386,839 | B2 | 7/2016 | Bonnin |
| 9,538,828 | B2 | 1/2017 | Tarling |

(Continued)

FOREIGN PATENT DOCUMENTS

| DE | 202015001288 | 3/2015 |
|---|---|---|
| EP | 2437631 | 12/2017 |

(Continued)

*Primary Examiner* — Jennifer C Chiang
(74) *Attorney, Agent, or Firm* — Wissing Miller LLP (57) ABSTRACT

A cosmetic package for applying a product including a cosmetic, care or pharmaceutical product onto the keratinous substrate comprises a receptacle and a cosmetic applicator. The cosmetic applicator comprises an applicator head, a stem and a closure. The applicator head further comprises a connecting member, an applying member and a rivet member. The connecting member further comprises a shank portion at a proximal portion thereof, a locking portion at a distal portion thereof, and a flexing portion which extends between the shank portion and the locking portion. The applying member rotates with respect to the stem and the flexible portion of the applicator head flexes during application of the cosmetic product onto the keratinous substrate.

14 Claims, 7 Drawing Sheets

(56) References Cited

U.S. PATENT DOCUMENTS

| | | |
|---|---|---|
| 9,642,440 B2 | 5/2017 | Thorpe |
| 9,827,589 B2 | 11/2017 | Daviot |
| 10,172,435 B2 | 1/2019 | Pires |
| 10,292,479 B2 * | 5/2019 | Thiebaut ................. A45D 34/04 |
| 10,477,942 B2 | 11/2019 | Badie |
| 10,582,753 B2 | 3/2020 | Villarreal |
| 10,881,183 B2 * | 1/2021 | Balestrini ............ A45D 34/045 |
| 2007/0181143 A1 * | 8/2007 | Montoli ................. A45D 34/04 |
| | | 132/320 |
| 2012/0224910 A1 | 9/2012 | Holloway |
| 2019/0000212 A1 | 6/2019 | Balestrini |
| 2019/0240108 A1 | 8/2019 | Chateauvert |
| 2020/0187628 A1 | 6/2020 | Shin |
| 2021/0212449 A1 * | 7/2021 | Dai .......................... A46D 3/00 |

FOREIGN PATENT DOCUMENTS

| | | |
|---|---|---|
| FR | 2908018 | 5/2008 |
| FR | 2979807 | 3/2013 |
| FR | 2995768 | 3/2014 |
| FR | 3036598 | 12/2016 |
| FR | 3060278 | 6/2018 |
| KR | 102019904 | 9/2019 |
| WO | 2007078769 | 7/2007 |

* cited by examiner

COSMETIC APPLICATOR WITH ROTATABLE APPLICATION SURFACE

This application claims priority under 35 U.S.C. § 119 to Indian Provisional Patent Application No. 202011005990, filed on Feb. 12, 2020. The disclosure of this application is incorporated herein by reference.

BACKGROUND

Field

The present disclosure generally relates to a cosmetic applicator for applying a product including a cosmetic, care or pharmaceutical product, onto keratinous substrate such as skin, lips, under eyes, eyebrows, eyelids, cheeks, nails or any other part of the body. In particular, the application relates to an applicator that includes an element for applying cosmetic products that is rotatable and to an applicator with such a rotatable element that is adapted to flex when pressed against the keratinous surface.

Description of the Related Art

Devices exist for dispensing cosmetic or medicinal products. Such devices usually consist of a receptacle carrying cosmetic or medicinal products and an applicator. For example, in the medical industry, applicators are employed for applying medicinal products, such as ointments, to portions of the body. In the cosmetics and personal care industries, applicators are used to apply lipstick, lip balm, skin creams, lotions, and other cosmetic products to portions of the body.

Applicators that are able to flex during the application of a cosmetic product to the skin are known. FR 2908018 and FR 2979807, describe applicators having a stem that has at least one elastically deformable flexible portion. The applicator element is fixed to the flexible portion. A rigid holding element may be fixed inside or around the flexible portion. This holding element improves the precision of care or makeup application. With such applicators, it is not always possible to achieve a completely satisfactory degree of comfort. In addition, they are not designed to massage an entire area of the face.

WO2007078769 relates to flocked cosmetic applicators having a mounting post connected to an applicator tip by a flexing element. The flexing element has a cutaway, reduced diameter portion, which may be provided by horizontal grooves formed on opposite sides of the flexing element, to provide flexibility by reducing its cross-sectional area. The applicator tip has a body and one or more flocked applicator surfaces. The design permits use of lower cost materials yet provides the sensation of softness to the user.

Rotary type cosmetic applicators are already known. U.S. Pat. No. 5,816,728 is known, that describes a mascara applicator in which the traditional brush has been replaced by several balls capable of rotating about themselves. The mascara gets trapped discontinuously between the balls, which cannot result in an application as uniform as is desired.

U.S. Pat. No. 2,034,416 is also known that describes a liquid applicator, such as a liquid deodorant, comprising a spongy application material capable of rotating about itself.

U.S. Pat. No. 6,811,340 discloses an applicator which comprises a longitudinal element with a manual gripping member fixed to its upper end and an element of application of the cosmetic product at its lower end, the application element cooperating with the lower end in rotation, and comprising a member for transferring or temporarily retaining the product.

The present disclosure aims to provide a cosmetic applicator comprising a flexible and rotatable applicator head, which is of simple and robust design. The cosmetic applicator according to the disclosure may be flexible, rotatable and precise to handle and may allow the user to access all parts of the skin easily and without constraint. Such a cosmetic applicator may be able to lightly massage areas of the face that are more delicate or more marked by tiredness.

SUMMARY

It is an object of the present disclosure to provide a cosmetic package that can be easily configured to contain a cosmetic product and a cosmetic applicator.

It is another object of the present disclosure to provide a cosmetic applicator which offers a comparatively large surface area, very simple to use, economic to manufacture and aesthetically pleasing. Accordingly, there is provided a cosmetic package comprising a receptacle and a cosmetic applicator.

The cosmetic applicator for applying a composition including a cosmetic, care or pharmaceutical composition onto a keratinous substrate comprises an applicator head, a stem and a closure. The applicator head further comprises a connecting member, an applying member and a rivet member. The connecting member further comprises a shank portion at a proximal portion thereof, a locking portion at a distal portion thereof, and a flexing portion which extends between the shank portion and the locking portion. The applying member is rotatable with respect to the stem and the flexible portion of the applicator head flexes during application of the cosmetic product onto the keratinous substrate. The applicator head extends along a longitudinal axis of the cosmetic applicator.

According to an aspect of the present disclosure, the shank portion of the applicator head is cylindrical in shape and is retained at a distal end of the stem for attaching the applicator head to the stem; and the closure is retained at a proximal end of the stem. More particularly, the distal end of the stem includes an interior longitudinal cavity for receiving and retaining the shank portion of the connecting member of the applicator head.

According to an embodiment of the present disclosure, the flexing portion of the connecting member is an hourglass shape. Further, the flexing portion of the connecting member has a first, proximal annular flange and a second, distal annular flange at two opposing ends of the hourglass shape. Further, the first, proximal annular flange of the flexing portion of the connecting member abuts the distal end of the stem while the second, distal annular flange of the flexing portion of the connecting member abuts a proximal end of the applying member. However, in alternate embodiments, the flexing portion of the connecting member may not be hourglass shape or may be of any other shape known in the art which allows flexing portion to be flexible.

Still further, the locking portion of the connecting member is hollow and is cylindrical in shape. However, in alternate embodiments, the locking portion of the connecting member may not be cylindrical in shape or may be of any other shape known in the art. According to an aspect of the present disclosure, the locking portion of the connecting member has a groove on its inner surface which is present substantially at its mid-length.

Still further, the applying member extends along the longitudinal axis of the applicator head. The applying member is hollow having a central bore. According to an aspect of the present disclosure, an outer surface of the applying member is uneven. Further, the applying member consists of raised/convex regions and depressed/concave regions which are present alternately on its outer surface. The uneven outer surface of the applying member is useful for applying the cosmetic product onto the bulged or recessed surfaces such as skin of face or neck. The uneven surface gives a massaging effect to the keratinous substrate and creates reservoir zones on the applying member. These reservoir zones carry the cosmetic product and help in transferring the cosmetic product onto the keratinous substrate when the applying member comes in contact with any of the keratinous substrate such as skin, lips, under eyes, eyebrows, eyelids, cheeks, nails or any other part of the body. However, in alternate embodiments, an outer surface of an applying member may not be uneven and may be comprised of a smooth outer surface.

According to an aspect of the present disclosure, the rivet member extends along the longitudinal axis of the applicator head. The rivet member has a first, proximal cylindrical portion, a locking flange at its distal end, and a second, distal cylindrical portion extending between the proximal cylindrical portion and the locking flange. The second, distal cylindrical portion is stepped out from the first, proximal cylindrical portion. Particularly, an outer diameter of the distal cylindrical portion is greater than an outer diameter of the proximal cylindrical portion of the rivet member. According to an aspect of the present disclosure, the proximal cylindrical portion of the rivet member has an annular protrusion which is present substantially at its mid-length. The distal cylindrical portion of the rivet member has a proximal annular bead and a distal annular bead. Further, the proximal annular bead is present at a proximal end of the distal cylindrical portion and the distal annular bead is spaced apart from the proximal annular bead. The distal annular bead is present at a certain length of the distal cylindrical portion preferably near the distal end of the rivet member.

According to an aspect of the present disclosure, the locking flange of the rivet member is present at a distal end of the rivet member. The locking flange extends in a transverse direction to the longitudinal axis of the cosmetic applicator. According to an embodiment of the present disclosure, the locking flange is of a bulbous shape. However, in alternate embodiments, the locking flange may be pointed or of any other shape known in the art.

The applying member is fitted to an outer circumferential surface of the rivet member. Particularly, the proximal annular bead and the distal annular bead on the distal cylindrical portion of the rivet member are received in the central bore of the applying member. Further, the rivet member and locking portion of the connecting member are coupled with each other inside the central bore of the applying member and wherein the groove on the inner surface of the locking portion of the connecting member receives the annular protrusion on the proximal cylindrical portion of the rivet member for fixing locking portion with the rivet member.

According to an aspect of the present disclosure, the connecting member is made of material softer than a material of the rivet member, so that the flexing portion of the connecting member is able to impart better flexing property and the rivet member allows easy rotation of the applying member by reducing the friction due to its rigidity. Further, outer diameters of the proximal cylindrical portion, the distal cylindrical portion of the rivet member and an outer diameter of the locking portion are smaller than an inner diameter of the central bore of the applying member so that the proximal cylindrical portion, the distal cylindrical portion of the rivet member and the locking portion are housed within the central bore of the applying member. Further, a diameter or a greatest width of the locking flange of the rivet member is greater than the inner diameter of the central bore of the applying member so that when the rivet member is inserted into the central bore of the applying member, the locking flange is retained outside the central bore of the applying member at the distal end of the applying member and thereby preventing the applying member from slipping out by locking an axial movement of the applying member towards a distal end of the applicator head. An axial movement of the applying member towards a proximal end of the applicator head is restricted by the distal annular flange of the flexing portion of the connecting member which abuts a proximal end of the applying member. Therefore, the axial movement of the applying member is locked at both its proximal end and distal end, and it is not separated from the rivet member and the connecting member of the applicator head. This way, the applying member always remains in a fitted condition with the connecting member and the rivet member.

According to an embodiment of the present disclosure, as the outer diameter of the distal cylindrical portion of the rivet member is smaller than the inner diameter of the central bore of the applying member, the applying member can easily rotate relative to the rivet member about the longitudinal axis of the cosmetic applicator. An inner circumferential surface of the applying member is in sliding contact with the proximal annular bead and the distal annular bead on the distal cylindrical portion of the rivet member so that the applying member free to rotate while remaining fixedly connected with the rivet member.

According to an embodiment of the present disclosure, the rivet member is longer than the length of the central bore of the applying member, so that the locking flange of the rivet member always remains exposed outside the distal end of the applying member. However, in alternate embodiments, the length of the rivet member may be shorter than the length of the central bore of the applying member. In such a case, a combined length of the rivet member and the locking portion of the connecting member may be longer than the length of the central bore of the applying member.

According to an aspect of the present disclosure, the flexing portion of the connecting member connects the shank portion and the locking portion. According to an embodiment of the present disclosure, the flexible portion is symmetrical about the longitudinal axis of the applicator head. However, in alternate embodiment, the flexible portion may not be symmetrical about the longitudinal axis of the applicator head.

According to an aspect of the present disclosure, the applicator head flexes with respect to the longitudinal axis of the stem. Particularly, the distal portion of the applicator head flexes due to the presence of the flexing portion when the applicator head is pressed against the keratinous substrate. According to some embodiments, the applicator head is able to flex away from the longitudinal axis of the stem in all radial directions (that is, along a circle about the longitudinal axis) to exert optimum pressure during application of the applicator head onto the keratinous substrate. When the application pressure ceases, the applicator head resiliently returns into its original position along the longitudinal axis of the cosmetic applicator. The presence of the flexible portion provides softness on the application, even with a relatively rigid applying member. Due to presence of the flexible portion in the applicator head, contact of the applicator head with the keratinous substrate is elastic, pleasant and comfortable. According to some embodiments, the user feels a massaging effect with as the cosmetic applicator is moved across the keratinous substrate. At the time of application, the contact between the applying member and the keratinous substrate is softened and the elasticity of the flexible portion may be beneficial for the application of the cosmetic product.

According to an embodiment of the present disclosure, the applying member is made of any of materials selected from the list of metal, ceramic, quartz, stone. However, in alternate embodiments, the applying member may be made from any other materials known in the art. According to an embodiment of the present disclosure, the connecting member which includes the shank portion, the flexing portion and the locking portion is preferably formed of an elastomeric material. According to some embodiments, the material may comprise thermoplastic materials; elastomers; thermoplastic elastomers; thermoplastic elastomer polyester such as HYTREL®. According to other embodiments, the connecting member is formed from any suitable polymeric material or any other material known in the art.

According to an embodiment of the present disclosure, the rivet member is made up of a rigid material. This material may be polyoxymethylene (POM). According to other embodiments, the material forming the rivet member is another rigid material known in the art.

In order to apply the cosmetic product onto the keratinous substrate such as skin, lips, eyelids, cheeks, nails or any other part of the body, the cosmetic applicator is dipped into the cosmetic product in the receptacle and then withdrawn from the receptacle with a quantity of cosmetic product collected on the applicator head. At the time of use of said cosmetic package, the user first separates the closure from the receptacle for withdrawing the cosmetic applicator. Upon withdrawing the cosmetic applicator from the state of being immersed in the cosmetic product, the cosmetic product is picked up and retained on the entire surface of the applying member. According to an embodiment of the present disclosure, the applying member is rotatable with respect to the stem and/or rivet member in order to bring substantially the entire outer surface of the applying member into contact with keratinous substrate without rotating the stem. As a consequence, more of the cosmetic product contained in the receptacle will be applied to the keratinous substrate than by devices in which the applying member is not rotatably coupled to the stem.

According to an aspect of the present disclosure, the receptacle is configured to contain a product including a cosmetic, care or pharmaceutical product. However, in alternate embodiments, the receptacle may include a separate inner reservoir to hold a volume of the product to be dispensed. The cosmetic, care or pharmaceutical product includes viscous cosmetics, mascara, eyebrow powder, lip gloss, hair color, cheek blush, skin care, under eye cosmetics, pharmaceutical and like products.

According to an embodiment of the present disclosure, the closure of the cosmetic package has threads on its inner surface which can be screwed onto threads, formed on an outer surface of a neck of the receptacle. However, in alternate embodiments, the closure may snap into place on the neck of the receptacle or any other type of mechanisms may be used to mate the closure to the receptacle.

According to an embodiment of the present disclosure, inserted in the neck of the receptacle is a wiper for wiping off excess cosmetic product from the cosmetic applicator. The wiper may comprise an annular bead on its outer surface for engaging into a corresponding annular groove formed on an inside surface of the neck of the receptacle. Further, the wiper may comprise a wiping orifice.

An applying member according to embodiments of the disclosure may be simple to use, and may allow for a homogeneous and sufficient application of the cosmetic product onto the keratinous substrate such as skin, lips, under eyes, eyebrows, eyelids, cheeks, nails or any other part of the body.

According to an embodiment, the cosmetic package is of an elongated cylindrical configuration. However, in alternate embodiments, the cosmetic package may be of an elongated square, polygonal configuration, oval, triangular, heart, or any other configuration known in the art.

According to an embodiment, the receptacle and the closure may be made of a rigid material like glass, metal, hard plastic or any other material known in the art. However, in alternate embodiments, the receptacle and the closure may be made of a flexible material like flexible polymeric material or any other material known in the art.

According to an embodiment of the present disclosure, the applicator head and the stem are fitted together by a snap fitment. In alternate embodiments, the applicator head and the stem may be fit together by friction fit, by gluing, crimping, magnetic engagement and the like.

According to an embodiment of the present disclosure, the stem has a longitudinal axis that is rectilinear. However, in alternate embodiments, the stem is curved. According to an embodiment of the present disclosure, the stem presents a cross-section that is circular. According to other embodiments the cross-section of the stem is oval, elliptical or polygonal, e.g. square, triangular or rectangular etc. The stem may be solid. According to other embodiments, the stem is hollow. In embodiments where the stem is not of circular cross-section, the closure may be fastened on the receptacle by snap-fastening or by some other means, without turning relative to said receptacle. Likewise, the wiper according to these embodiments has a non-circular wiper orifice cross section that is complementary to the cross section of the stem.

According to an embodiment of the present disclosure, the applicator head is made, at least in part, from a material that is more flexible than a material from which the stem is made.

According to an embodiment of the present disclosure, an outer surface of the applying member of an applicator head is covered with an application element that may include flocked fibers. The fibers may comprise materials known for use as flocking material, including but not limited to nylon, polyester or natural fiber. The fibers may be applied with an adhesive, such as an epoxy, to the surface to be flocked. The flocking finish to the outer surface of the applying member may be achieved by an appropriately chosen known technique, such as electrostatic flocking. According to some embodiments, the outer surface of the applying member before being flocked is smooth on its entire surface. That is, the outer surface of the applying member before being flocked may have no surface textures over the entire surface thereof and may be smooth and slippery. According to other embodiments, the surface of the applying member has a wrinkle finish or a matte finish before being flocked.

According to some embodiments, the flocking process takes place in an electrostatic field, which results in a selected orientation of the fibers. The flock on the outer surface of the applying member provides a convenient "reservoir" which can hold a small amount of the cosmetic product adequate for one or two applications. In alternate embodiments, the outer surface of the applying member may include injection molded fibers, projections or grooves which are capable of holding the cosmetic product. According to an embodiment of the present disclosure, the outer surface of the applying member is covered by a flock coating. However, in alternate embodiments, the outer surface of the applying member may not be covered by a flock coating.

According to some embodiments, there is disclosed an applicator head comprising a connecting member, the connecting member comprising a distal annular flange; an applying member, the applying member comprising an outer surface and a central bore; and a rivet member, the rivet member comprising a locking flange at a distal end of the rivet member and a distal cylindrical portion extending from a proximal portion of the rivet member to the locking flange, wherein the proximal portion of the rivet member is connected with a distal portion of the connecting member, wherein the distal cylindrical portion extends through the central bore of the applying member, and wherein the applying member is rotatable about the distal cylindrical portion and is captive between the locking flange of the rivet member and the distal annular flange of the connecting member. The connecting member may further comprises a locking portion, wherein the rivet member further comprises a proximal cylindrical portion and an annular protrusion disposed on the proximal cylindrical portion, and wherein the rivet member and connecting member are connected by engagement between the locking portion and the annular protrusion.

A proximal portion of the connecting member may comprise a shank portion at the proximal end of the connecting member and a flexing portion, wherein the rivet member is connected with the connecting member at a distal end of the flexing portion. The connecting member may be disposed along a longitudinal axis and the flexing portion may allow the rivet member and applying member to flex away from the longitudinal axis when force is applied to the applying member.

According to one aspect the flexing portion is radially symmetric about the longitudinal axis and the flexing portion allows the rivet and applying member to flex away from the longitudinal axis in all radial directions. The flexing portion may have an hourglass shape. The flexing portion may comprise an elastomeric material.

The distal cylindrical portion of the applicator head may comprise one or more annular beads extending about a circumference of the distal cylindrical portion and the one or more beads may be in sliding contact with an inner surface of the central bore.

According to another aspect the applying member comprises an outer surface, wherein the outer surface comprises one or more convex regions and one or more concave regions. According to another aspect the applying member comprises an outer surface, wherein a shape of the outer surface comprises an ovoid. According to yet another aspect, the applying member comprises an outer surface, wherein the outer surface comprises application elements. The application elements may comprise flocked fibers.

According to other embodiments, the applicator head comprises a cosmetic packaging, the cosmetic packaging comprising a stem, wherein a distal end of the stem comprises an interior longitudinal cavity, wherein the shank portion of the connecting member is received in the longitudinal cavity. The cosmetic packaging may further comprise a receptacle adapted to hold a cosmetic product, a neck forming a portion of the receptacle, and a wiper disposed in the neck, wherein the applicator head and stem are moved into and out from the receptacle through the wiper, and wherein, when the applicator head is inserted into the receptacle, cosmetic product adheres to the applicator head and, when the applicator head is moved out from the receptacle the wiper wipes off excess cosmetic product from the applicator head.

It will be understood that the foregoing is only illustrative of the principles of the disclosure, and that various modifications can be made by those skilled in the art without departing from the scope and spirit of the disclosure. For example, the shapes and/or sizes of various components can be different from the shapes and sizes described herein. As another example, the materials used for various components can be different from those mentioned specifically herein.

Other objects, features, and advantages of the present disclosure will become clear from the following description of the preferred embodiments when the same is read in conjunction with the accompanying drawings.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

To facilitate understanding, identical reference numerals have been used, where possible, to designate identical elements that are common to the figures. It is to be noted, however, that the appended drawings illustrate only typical embodiments of this disclosure and are therefore not to be considered limiting of its scope, for the disclosure may admit to other equally effective embodiments.

DETAILED DESCRIPTION

Throughout this specification, the terms "comprise," "comprises," "comprising" and the like, shall consistently mean that a collection of objects is not limited to those objects specifically recited.

Figure 1:
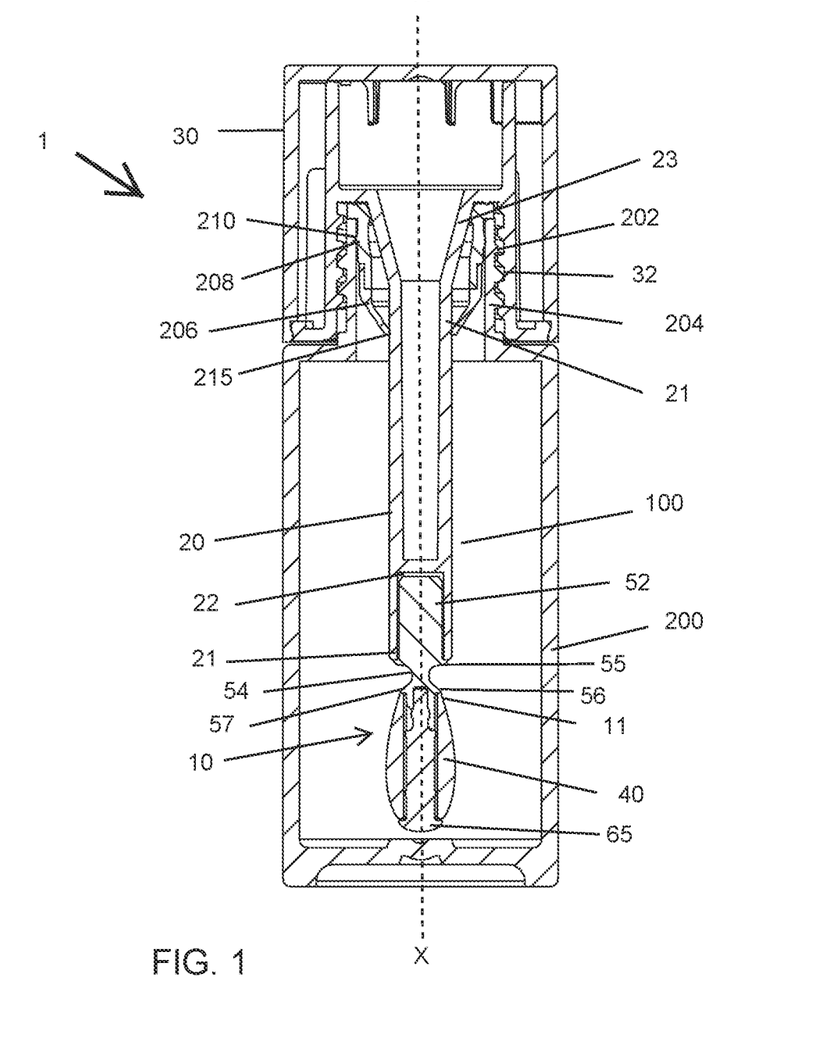
FIG. 1 illustrates a longitudinal cross sectional view of a cosmetic package in a closed position according to an embodiment of the present disclosure.

FIG. 1 illustrates a longitudinal sectional view of a cosmetic package 1 according to an embodiment of the present disclosure. The cosmetic package 1 comprises a receptacle 200 and a cosmetic applicator 100. The receptacle 200 is configured to contain a product (not shown) including a cosmetic, care or pharmaceutical product. However, in alternate embodiments, the receptacle 200 may include a separate inner reservoir to hold a volume of the product to be dispensed. The cosmetic, care or pharmaceutical product includes viscous cosmetics, mascara, eyebrow powder, lip gloss, hair color, cheek blush, skin care, under eye cosmetics, pharmaceutical and like products. According to an embodiment, the cosmetic applicator 100 comprises an applicator head 10, a stem 20 and a closure 30. The closure 30 of the cosmetic package 1 has threads 32 on its inner surface which can be screwed onto threads 202, formed on an outer surface of a neck 204 of the receptacle 200. However, in alternate embodiments, the closure 30 may snap into place on the neck 204 of the receptacle 200 or any other type of mechanisms may be used to mate the closure 30 to the receptacle 200. As shown in FIG. 1, the applicator head 10 extends along a longitudinal axis X-X of the cosmetic applicator 100.

Figure 2:
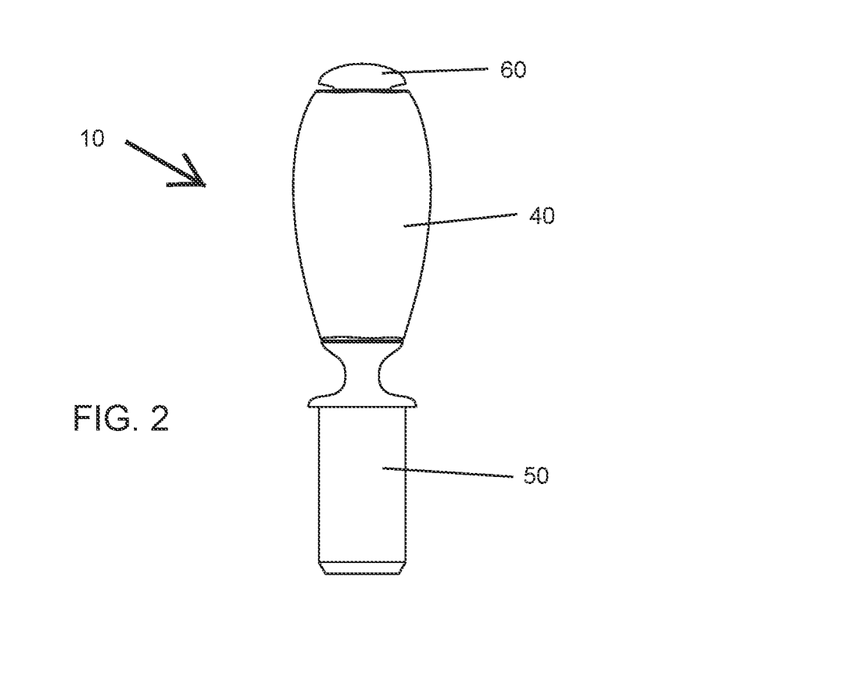
FIG. 2 illustrates a front view of an applicator head of a cosmetic applicator of the cosmetic package of FIG. 1.
Figure 3:
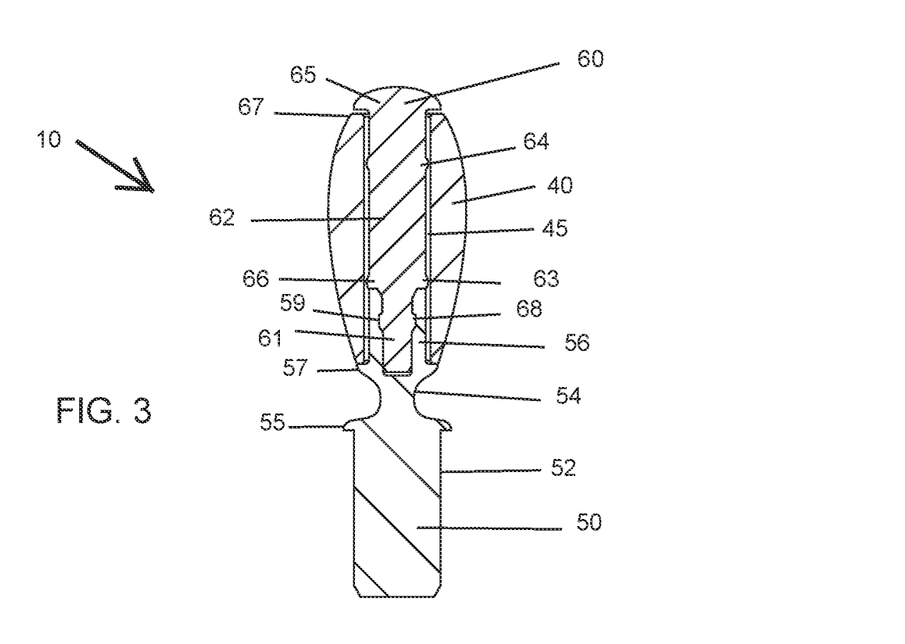
FIG. 3 illustrates a cross sectional view of the applicator head of FIG. 2.
Figure 7:
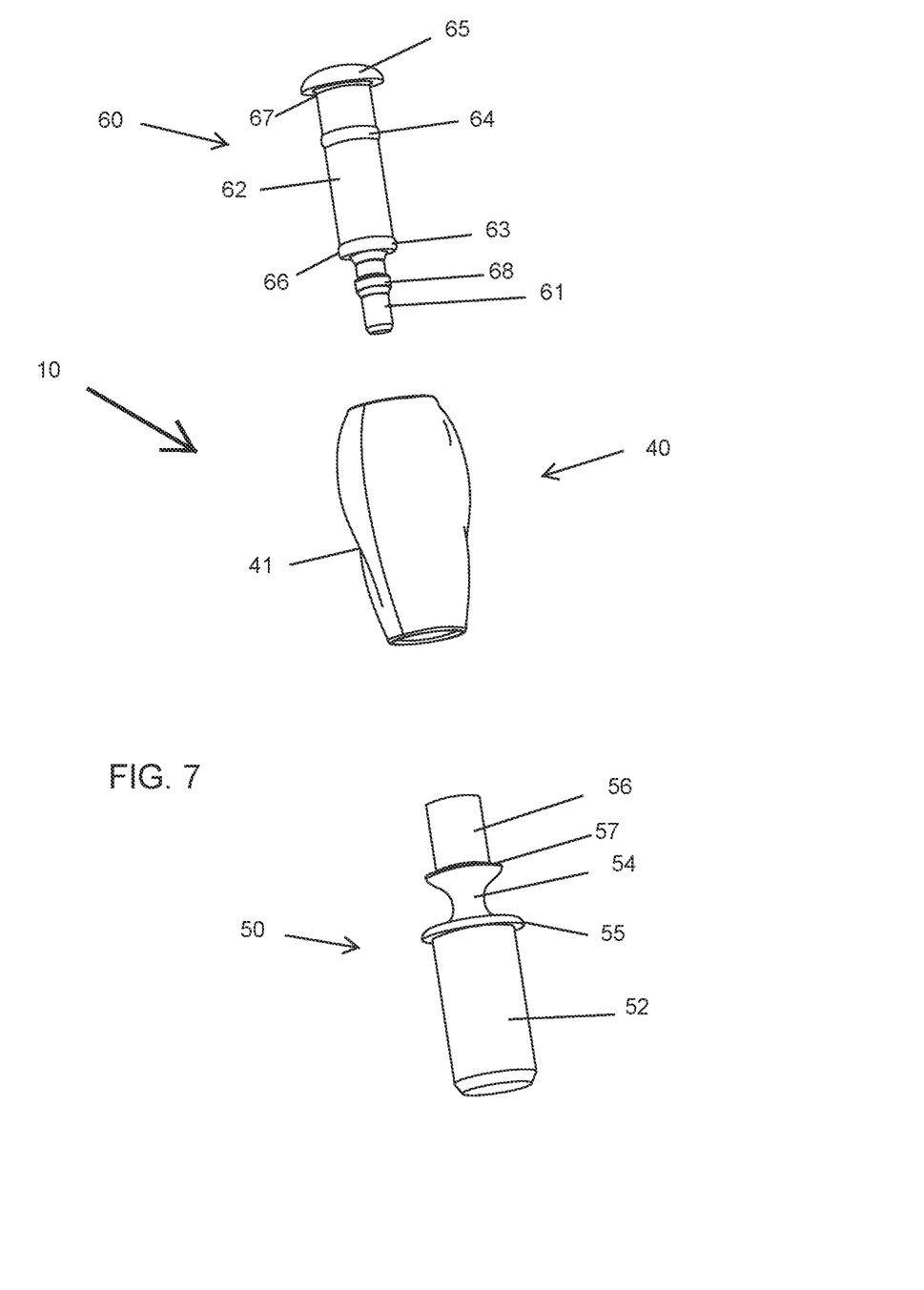
FIG. 7 illustrates an exploded view of the applicator head of FIG. 2.

Inserted in the neck 204 of the receptacle 200 is a wiper 206 for wiping off excess cosmetic product from the cosmetic applicator 100. The wiper 206 also comprises an annular bead 208 on its outer surface for engaging into a corresponding annular groove 210 formed on an inside surface of the neck 204 of the receptacle 200. Further, the wiper 206 comprises a wiping orifice 215. As shown in FIG. 2, the applicator head 10 comprises an applying member 40, a connecting member 50 and a rivet member 60. As shown in FIGS. 3 and 7, the connecting member 50 further comprises a shank portion 52 at a proximal portion thereof, a locking portion 56 at a distal portion thereof, and a flexing portion 54 which extends between the shank portion 52 and the locking portion 56. The shank portion 52 and the locking portion 56 are connected by the flexing portion 54. Further as shown in FIGS. 1 and 2, the shank portion 52 is cylindrical in shape and is retained at a distal end 21 of the stem 20 for attaching the applicator head to the stem; and the closure 30 is retained at a proximal end 23 of the stem 20. The distal end 21 of the stem 20 includes an interior longitudinal cavity 22 for receiving and retaining the shank portion 52 of the connecting member 50 of the applicator head 10.

As shown in FIGS. 3 and 7, the flexing portion 54 of the connecting member 50 has a proximal annular flange 55 and a distal annular flange 57. Further, as shown in FIG. 1, the proximal annular flange 55 of the flexing portion 54 of the connecting member 50 abuts the distal end 21 of the stem 20 while the distal annular flange 57 of the flexing portion 54 of the connecting member 50 abuts a proximal end 11 of the applying member 40. As shown in FIG. 3, the locking portion 56 of the connecting member 50 is hollow and is cylindrical in shape. However, in alternate embodiments, the locking portion 56 of the connecting member 50 may not be cylindrical in shape or may be of any other shape known in the art. According to an aspect of the present disclosure, the locking portion 56 of the connecting member 50 has a groove 59 on its inner surface which is present substantially at its mid-length, refer FIG. 3.

Figure 4:
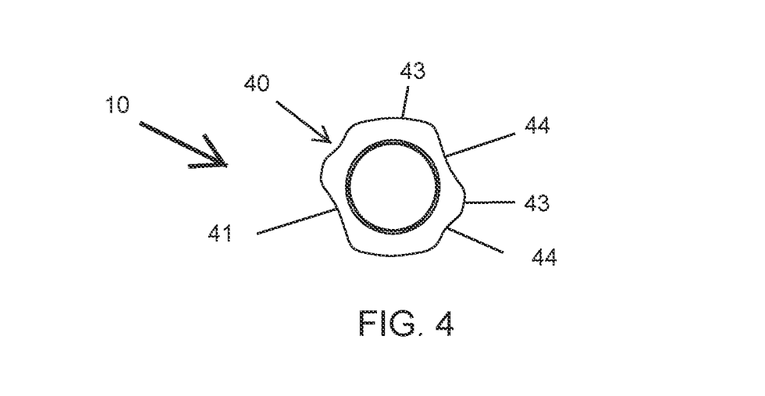
FIG. 4 illustrates a top view of the applicator head of FIG. 2.
Figure 5:
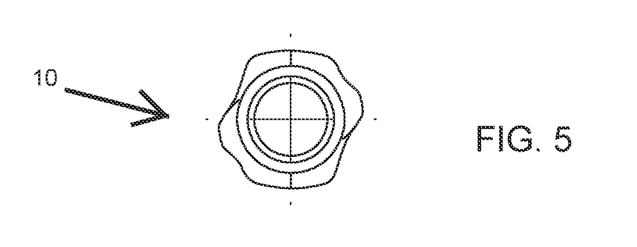
FIG. 5 illustrates a bottom view of the applicator head of FIG. 2.
Figure 6:
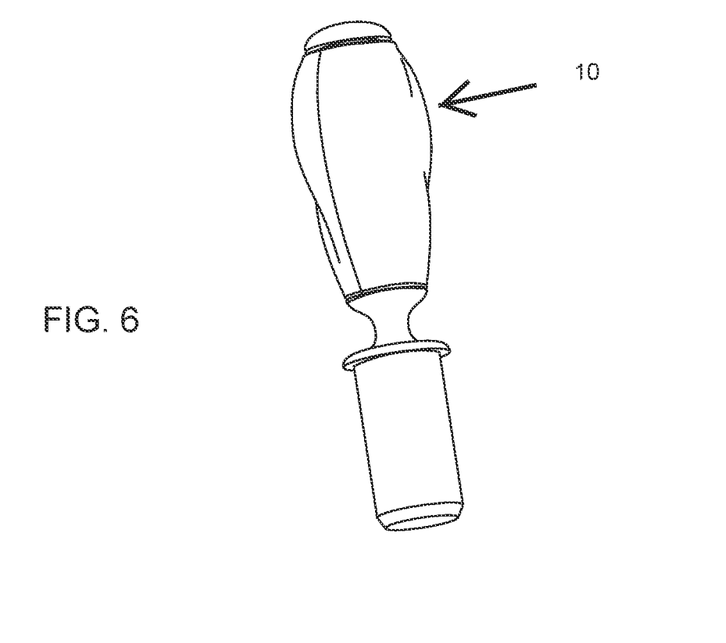
FIG. 6 illustrates a perspective view of the applicator head of FIG. 2.
Figure 8:
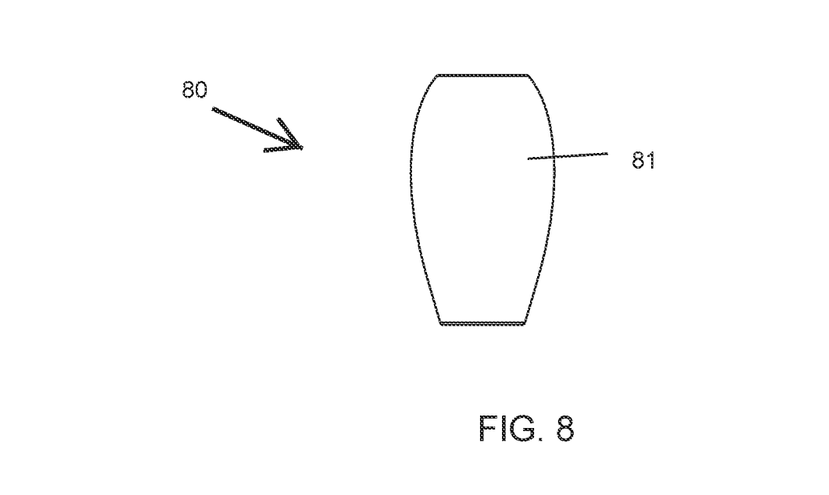
FIG. 8 illustrates an applying member of an applicator head according to an alternate embodiment of the present disclosure.
Figure 9:
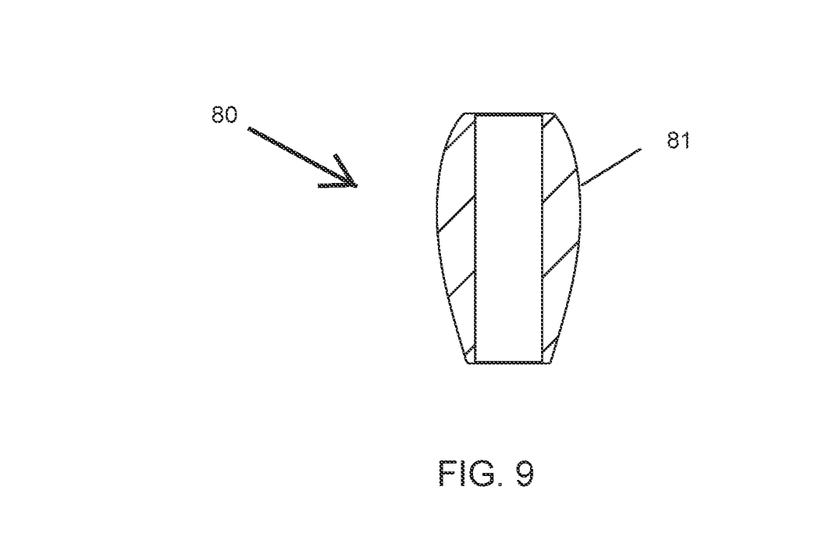
FIG. 9 illustrates a cross sectional view of the applying member of FIG. 8.

Further, the applying member 40 extends along the longitudinal axis X-X of the applicator head 10. The applying member 40 is hollow having a central bore 45. As shown in FIG. 7, an outer surface 41 of the applying member 40 is uneven. Further, as shown in FIG. 4, the applying member 40 consists of raised/convex regions 43 and depressed/concave regions 44 which are present alternately on its outer surface 41. The uneven outer surface 41 of the applying member 40 is useful for applying the cosmetic product onto the bulged or recessed surfaces such as skin of face or neck. The uneven surface gives a massaging effect to the keratinous substrate and creates reservoir zones on the applying member 40. These reservoir zones carry the cosmetic product and helps in transferring the cosmetic product onto the keratinous substrate when the applicator head 10 comes in contact with any of the keratinous substrate such as skin, lips, under eyes, eyebrows, eyelids, cheeks, nails or any other part of the body. However, in alternate embodiments, as shown in FIGS. 8 and 9, an outer surface 81 of an applying member 80 may not be uneven and may be comprised of a smooth outer surface 81. According to some embodiments, the shape of outer surface 81 comprises a smooth ovoid.

As shown in FIGS. 3 and 7, the rivet member 60 extends along the longitudinal axis X-X of the applicator head 10. The rivet member 60 has a proximal cylindrical portion 61, a locking flange 65 at its distal end, and a distal cylindrical portion 62 extending between the proximal cylindrical portion 61 and the locking flange 65. The distal cylindrical portion 62 is step out from the proximal cylindrical portion 61. Particularly, an outer diameter of the distal cylindrical portion 62 is more than an outer diameter of the proximal cylindrical portion 61 of the rivet member 60. According to an aspect of the present disclosure, the proximal cylindrical portion 61 of the rivet member 60 has an annular protrusion 68 which is present substantially at its mid-length. The distal cylindrical portion 62 of the rivet member 60 has a proximal annular bead 63 and a distal annular bead 64. The proximal annular bead 63 is present at or near a proximal end 66 of the distal cylindrical portion 62 and the distal annular bead 64 is spaced apart from the proximal annular bead 63. The distal annular bead 64 is present at a certain length of the distal cylindrical portion 62 preferably near the distal end of the rivet member 60. The locking flange 65 of the rivet member 60 is present at a distal end of the rivet member 60. The locking flange 65 extends in a transverse direction to the longitudinal axis X-X of the cosmetic applicator 100 (refer FIG. 1).

According to an embodiment of the present disclosure, the locking flange 65 is of a bulbous shape. However, in alternate embodiments, the locking flange 65 may be pointed or of any other shape known in the art. As shown in FIG. 3, the applying member 40 is fitted to an outer circumferential surface of the rivet member 60. Particularly, the proximal annular bead 63 and the distal annular bead 64 on the distal cylindrical portion 62 of the rivet member 60 are received in the central bore 45 of the applying member 40. According to an aspect of the present disclosure, the connecting member 50 is made of material softer than a material of the rivet member 60, so that the flexing portion 54 of the connecting member 50 is able to impart better flexing property and the rivet member 60 allows easy rotation of the applying member 40 by reducing the friction due to its rigidity.

As seen inn FIG. 3, the rivet member 60 and locking portion 56 are coupled with each other inside the central bore 45 of the applying member 40 and wherein the groove 59 on the inner surface of the locking portion 56 of the connecting member 50 receives the annular protrusion 68 on the proximal cylindrical portion 61 of the rivet member 60 for fixing locking portion 56 with the rivet member 60. Further, referring to FIG. 3, outer diameters of the proximal cylindrical portion 61, the distal cylindrical portion 62 of the rivet member 60 and an outer diameter of the locking portion 56 are smaller than an inner diameter of the central bore 45 of the applying member 40 so that the proximal cylindrical portion 61, the distal cylindrical portion 62 of the rivet member 60 and the locking portion 56 are housed within the central bore 45 of the applying member 40. Further, a diameter or a greatest width of the locking flange 65 of the rivet member 60 is greater than the inner diameter of the central bore 45 of the applying member 40 so that when the rivet member 60 is inserted into the central bore 45 of the applying member 40, the locking flange 65 is retained outside the central bore 45 of the applying member 40 at the distal end 67 of the applying member 40 and thereby preventing the applying member 40 from disengaging with the applicator head by locking an axial movement of the applying member 40 towards a distal end of the applicator head 10. An axial movement of the applying member 40 towards a proximal end of the applicator head 10 is restricted by the distal annular flange 57 of the flexing portion 54 of the connecting member 50 which abuts a proximal end 11 of the applying member 40 (refer FIG. 1). Therefore, the axial movement of the applying member 40 is locked at both its proximal end 11 and distal end 67, and it is not separated from the rivet member 60 and the connecting member 50 of the applicator head 10. This way, the applying member 40 always remains in a fitted condition with the connecting member 50 and the rivet member 60. According to an embodiment of the present disclosure, as the outer diameter of the distal cylindrical portion 62 of the rivet member 60 is smaller than the inner diameter of the central bore 45 of the applying member 40, the applying member 40 can easily rotate relative to the rivet member 60 about the longitudinal axis X-X of the cosmetic applicator 100. An inner circumferential surface of the applying member 40 is in contact with the proximal annular bead 63 and the distal annular bead 64 on the distal cylindrical portion 62 of the rivet member 60 so that the applying member 40 is rotated. Therefore, the applying member 40 is effectively rotated without getting separated from the rivet member 60. According to an embodiment of the present disclosure, the rivet member 60 is longer than the length of the central bore 45 of the applying member 40, so that the locking flange 65 of the rivet member 60 always remains exposed outside the distal end 67 of the applying member 40. However, in alternate embodiments, the length of the rivet member 60 may be shorter than the length of the central bore 45 of the applying member 40. In such cases, a combined length of the rivet member 60 and the locking portion 56 of the connecting member 50 may be longer than the length of the central bore 45 of the applying member 40.

As shown in FIGS. 3 and 7, the flexing portion 54 of the connecting member 50 connects the shank portion 52 and the locking portion 56. According to an embodiment of the present disclosure, the flexible portion 54 is symmetrical about the longitudinal axis X-X of the applicator head 10. However, in alternate embodiment, the flexible portion 54 may not be symmetrical about the longitudinal axis X-X of the applicator head 10. According to an embodiment of the present disclosure, the flexing portion 54 of the connecting member 50 is an hourglass shape. However, in alternate embodiments, the flexing portion 54 of the connecting member 50 may not be hourglass shape or may be of any other shape known in the art.

Figure 11A:
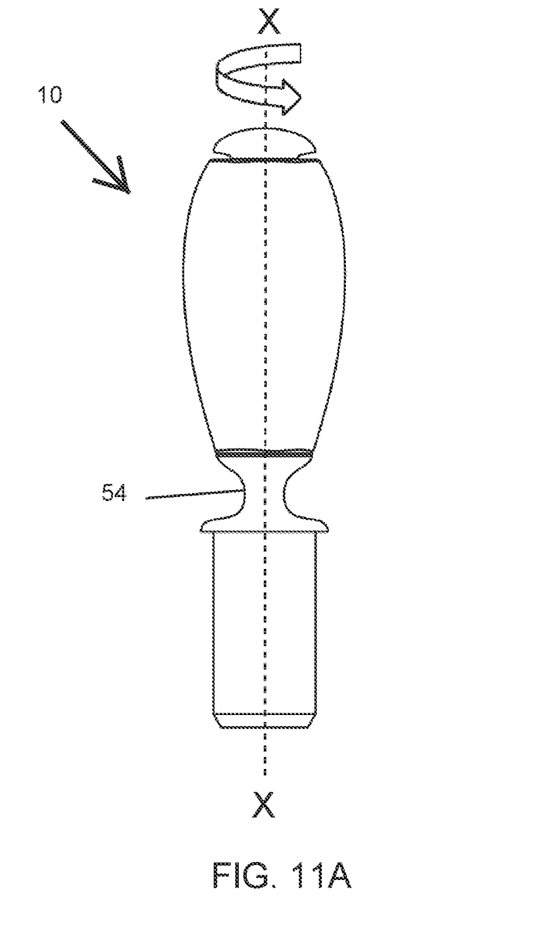
FIG. 11A illustrates a front view of the applicator head of FIG. 2, showing rotation of the applying member of the applicator head.
Figure 11B:
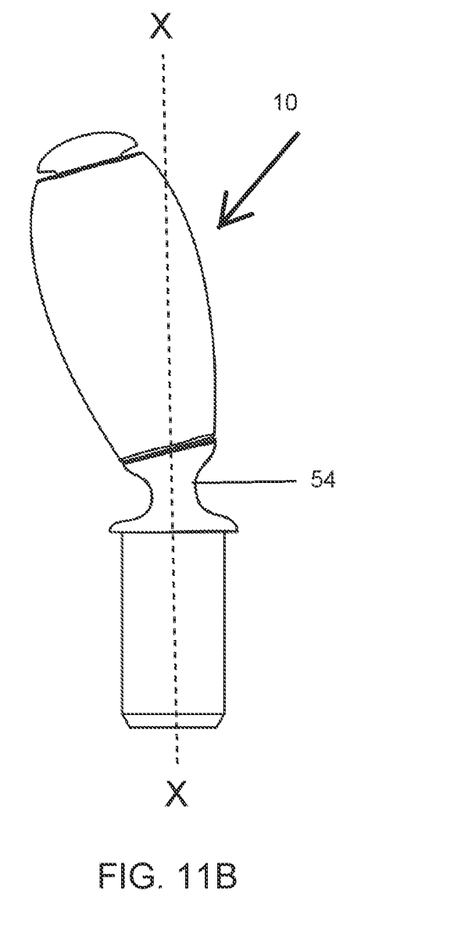
FIG. 11B illustrates a front view of the applicator head of FIG. 11A showing the applicator head in a flexed state.

As shown in FIG. 11B, the applicator head 10 flexes with respect to the longitudinal axis X-X of the stem 20. Particularly, the distal portion of the applicator head 10 flexes due to the presence of the flexing portion 54 during its application against the keratinous substrate. More particularly, when application pressure is applied the applicator head 10 flexes away from the longitudinal axis to exert optimum pressure during application of the applicator head 10 onto the keratinous substrate. According to some embodiments, the applicator head 10 can flex in any direction away from the axis, that is, along a full circle about the longitudinal axis. When the application pressure ceases, the applicator head 10 automatically returns into its original position that is the longitudinal axis X-X of the cosmetic applicator 100 as shown in FIG. 11A due to resilience of flexing portion 54. The presence of the flexible portion 54 provides softness and tonicity for the application, even with a relatively rigid applying member 40. Due to presence of the flexible portion 54 in the applicator head 10, contact of the applicator head 10 with the keratinous substrate is elastic, pleasant and comfortable. The user thus feels a massaging effect as the cosmetic applicator 100 is moved across the user's skin. At the time of application, the contact between the applying member 40 and the keratinous substrate is softened and the elasticity of the flexible portion 54 proves to be beneficial for the application of the cosmetic product.

According to an embodiment of the present disclosure, the applying members 40 and 80 are made of any of materials selected from the list of metal, ceramic, quartz, stone. However, in alternate embodiments, the applying members 40 and 80 may be made from any other materials known in the art.

According to an embodiment of the present disclosure, the connecting member 50 which includes the shank portion 52, the flexing portion 54 and the locking portion 56 is preferably formed of an elastomeric material. The elastomeric material is selected from one or more of thermoplastic materials; elastomers; thermoplastic elastomers; thermoplastic elastomer polyester such as HYTREL®. However, in alternate embodiments, the connecting member 50 may be formed from any suitable polymeric material or any other material known in the art. According to an embodiment of the present disclosure, the rivet member 60 is made up of a rigid material. According to one embodiment, rivet member 60 is formed from polyoxymethylene (POM). However, in alternate embodiments, the rivet member 60 may be made from any other rigid material known in the art.

At the time of use of said cosmetic package 1, the user first separates the closure 30 from the receptacle 200. In order to apply the cosmetic product onto the keratinous substrate such as skin, lips, eyelids, cheeks, nails or any other part of the body, the cosmetic applicator 100 is dipped into the cosmetic product in the receptacle 200 and then can be applied by the applicator head 10. Upon withdrawing the cosmetic applicator 100 from the state of being immersed in the cosmetic product (the state shown in FIG. 1), the cosmetic product is picked up and retained on the entire surface of the applying member 40. According to an embodiment of the present disclosure, the applying members 40, 80 are rotatable with respect to the stem 20 in order to bring substantially the entire outer surfaces 41, 81 of the applying members 40, 80 into contact with keratinous substrate without rotating the stem 20. As a consequence, more of the cosmetic product contained in the receptacle 200 will be applied to the keratinous substrate than by devices in which the applying member is not rotatably coupled to the stem.

The applying members 40, 80 are therefore particularly simple to use, and allows for a homogeneous and sufficient application of the cosmetic product onto the keratinous substrate such as skin, lips, under eyes, eyebrows, eyelids, cheeks, nails or any other part of the body.

According to an embodiment and as shown in FIG. 1, the cosmetic package 1 is of an elongated cylindrical configuration. However, in alternate embodiments, the cosmetic package 1 may be of an elongated square, polygonal configuration, oval, triangular, heart, or any other configuration known in the art.

According to an embodiment, the receptacle 200 and the closure 30 may be made of a rigid material like glass, metal, hard plastic or any other material known in the art. However, in alternate embodiments, the receptacle 200 and the closure 30 may be made of a flexible material like flexible polymeric material or any other material known in the art. According to an embodiment of the present disclosure, the applicator head 10 and the stem 20 are fitted together by a snap fitment. However in alternate embodiments, the applicator head 10 and the stem 20 may be fit together by friction fit, by gluing, crimping, magnetic engagement and the like.

According to an embodiment of the present disclosure, the stem 20 can have the longitudinal axis X-X that is rectilinear as shown. However, in alternate embodiments, it could be curved. According to an embodiment of the present disclosure, the stem 20 presents a cross-section that is circular. According to other embodiments, the cross section of the stem has a non-circular cross section that may be oval, elliptical or polygonal, e.g. square, triangular or rectangular etc. The stem 20 can be solid as shown, or, in a variant, it could be hollow. When the stem 20 is not of circular cross-section, the closure 30 can possibly by fastened on the receptacle 200 by snap-fastening or by some other means, without turning relative to said receptacle 200. The wiper 206 can thus present a non-circular wiper orifice 215 of section that is complementary to the section of the stem 20. According to an embodiment of the present disclosure, the applicator head 10 can be made, at least in part, from a material that is more flexible than a material from which the stem 20 is made.

Figure 10:
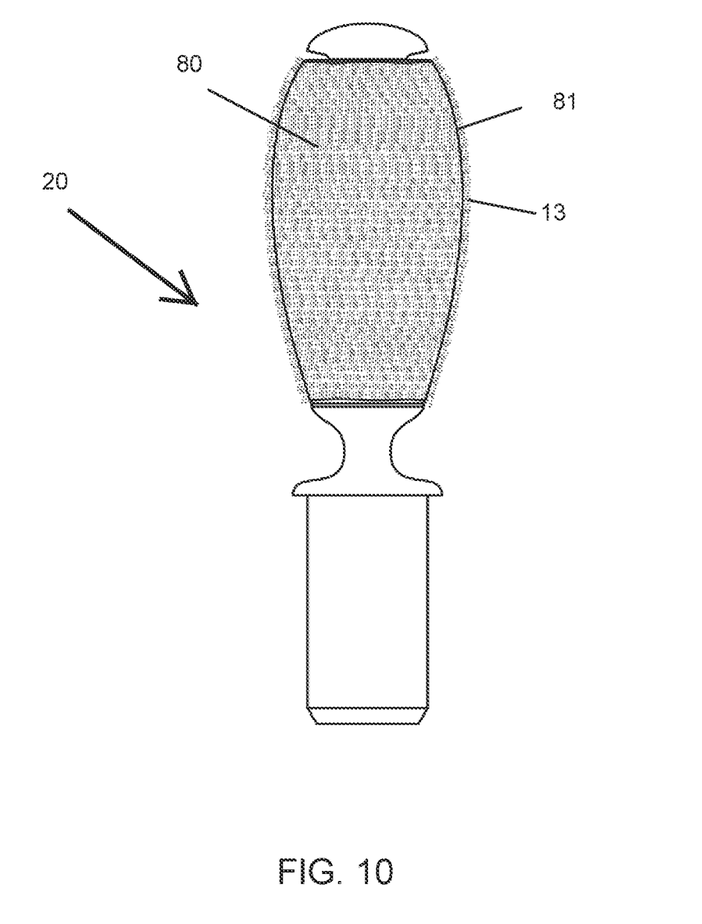
FIG. 10 illustrates a front view of the applicator head of FIG. 2 with a flocking on an applying member of the applicator head.

According to an embodiment of the present disclosure, an outer surface 81 of the applying member 80 of an applicator head 10 is covered with application element 13 which may include flocked fibers (refer FIG. 10). Briefly, the fibers for flocking which may be of any commonly used material, such as nylon, polyester or any natural fiber are applied with an adhesive, such as an epoxy, to the surface to be flocked. The flocking finish to the outer surface 81 of the applying member 80 may be achieved by an appropriately chosen known technique, such as electrostatic flocking. According to some embodiments, the outer surface 81 of the applying member 80 before being flocked is smooth on its entire surface. That is, according to some embodiments the outer surface 81 of the applying member 80 before being flocked has no surface textures and is smooth and slippery. According to other embodiments, the surface of applying member has a wrinkle finish or a matte finish before flocking is applied.

Preferably, the flocking process takes place in an electrostatic field, which results in the proper orientation of the fibers. The flock on the outer surface 81 of the applying member 80 provides a convenient "reservoir" which can hold a small amount of the cosmetic product adequate for one or two applications. In alternate embodiments, the outer surface 81 of the applying member 80 may include injection molded fibers, projections or grooves which are capable of holding the cosmetic product. According to an embodiment of the present disclosure, the outer surface 81 of the applying member 80 is covered by a flock coating. However, in alternate embodiments, the outer surface 81 of the applying member 80 may not be covered by a flock coating.

The present disclosure is not limited to, the broadest in accordance with the basic idea disclosed herein. It should be interpreted as having a range. Skilled artisans may implement the pattern of the non-timely manner by combining, replacement of the disclosed embodiments shape, this would also do not depart from the scope of the disclosure. In addition, those skilled in the art may readily change or modifications to the disclosed embodiments, based on the present specification, such changes or modifications also belong to the scope of the present disclosure will be apparent.

Although, the present disclosure has been described with reference to exemplary embodiments, it is not limited thereto. Those skilled in the art will appreciate that numerous changes and modifications may be made to the preferred embodiments of the present disclosure and that such changes and modifications may be made without departing from the true spirit of the present disclosure. It is therefore intended that the appended claims be construed to cover all such equivalent variations as fall within the true spirit and scope of the present disclosure.

While the foregoing is directed to embodiments of the present disclosure, other and further embodiments of the disclosure may be devised without departing from the basic scope thereof, and the scope thereof is determined by the claims that follow.

What is claimed is:

1. An applicator head comprising;
  a connecting member, the connecting member comprising a distal annular flange;
  an applying member, the applying member comprising an outer surface and a central bore; and
  a rivet member, the rivet member comprising a locking flange at a distal end of the rivet member and a distal cylindrical portion extending from a proximal portion of the rivet member to the locking flange, wherein the proximal portion of the rivet member is connected with a distal portion of the connecting member,
  wherein the distal cylindrical portion extends through the central bore of the applying member, and wherein the applying member is rotatable about the distal cylindrical portion and is captive between the locking flange of the rivet member and the distal annular flange of the connecting member.

2. The applicator head of claim 1, wherein the connecting member further comprises a locking portion, wherein the rivet member further comprises a proximal cylindrical portion and an annular protrusion disposed on the proximal cylindrical portion, and wherein the rivet member and connecting member are connected by engagement between the locking portion and the annular protrusion.

3. The applicator head of claim 1, wherein a proximal portion of the connecting member comprises a shank portion at a proximal end of the connecting member and a flexing portion, wherein the rivet member is connected with the connecting member at a distal end of the flexing portion.

4. The applicator head of claim 3, wherein the connecting member is disposed along a longitudinal axis and wherein the flexing portion allows the rivet member and applying member to flex away from the longitudinal axis when force is applied to the applying member.

5. The applicator head of claim 4, wherein the flexing portion is radially symmetric about the longitudinal axis and wherein the flexing portion allows the rivet and applying member to flex away from the longitudinal axis in all radial directions.

6. The applicator head of claim 5, wherein the flexing portion has an hourglass shape.

7. The applicator head of claim 3, wherein the flexing portion comprises an elastomeric material.

8. The applicator head of claim 1, wherein the distal cylindrical portion comprises one or more annular beads extending about a circumference of the distal cylindrical portion and wherein the one or more beads are in sliding contact with an inner surface of the central bore.

9. The applicator head of claim 1, wherein the applying member further comprises an outer surface, wherein the outer surface comprises one or more convex regions and one or more concave regions.

10. The applicator head of claim 1, wherein the applying member further comprises an outer surface, wherein a shape of the outer surface comprises an ovoid.

11. The applicator head of claim 1, wherein the applying member further comprises an outer surface, wherein the outer surface comprises application elements.

12. The applicator head of claim 11, wherein the application elements comprise flocked fibers.

13. The applicator head of claim 3, further comprising a cosmetic packaging, the cosmetic packaging comprising a stem, wherein a distal end of the stem comprises an interior longitudinal cavity, wherein the shank portion of the connecting member is received in the longitudinal cavity.

14. The applicator head of claim 13, wherein the cosmetic packaging further comprises a receptacle adapted to hold a cosmetic product, a neck forming a portion of the receptacle, and a wiper disposed in the neck, wherein the applicator head and stem are moved into and out from the receptacle through the wiper, and wherein, when the applicator head is inserted into the receptacle, cosmetic product adheres to the applicator head and, when the applicator head is moved out from the receptacle the wiper wipes off excess cosmetic product from the applicator head.

* * * * *